Sept. 6, 1938. L. BURBANK Plant Pat. 291
PEACH TREE
Filed Dec. 15, 1937
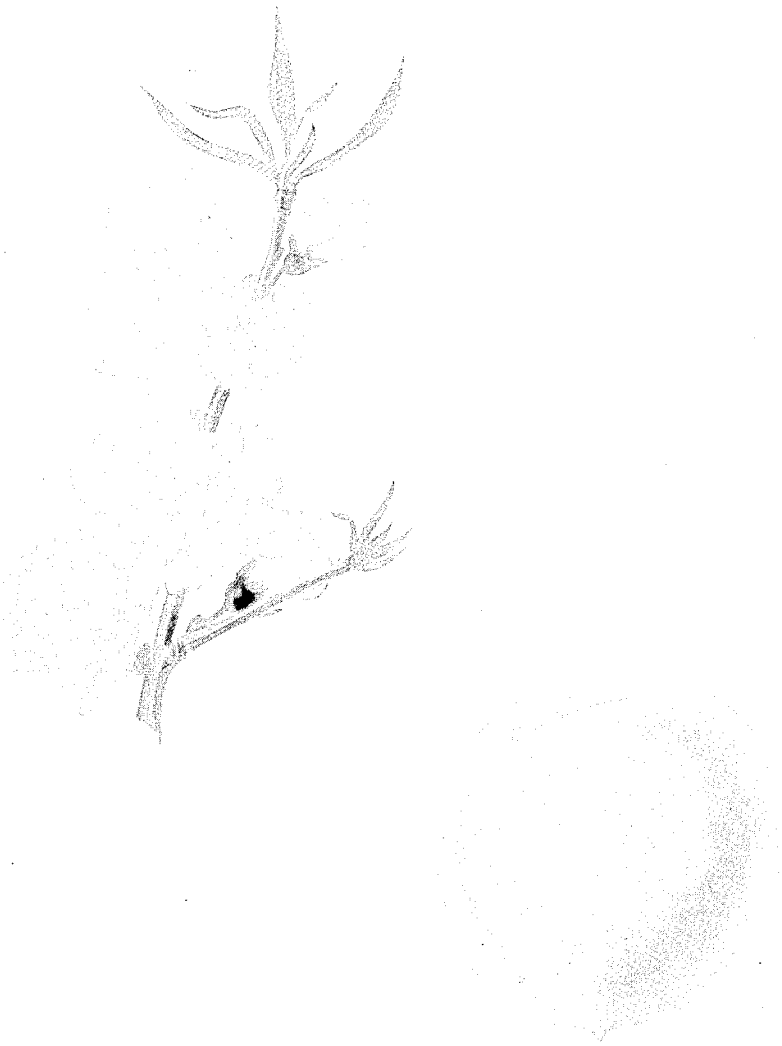
Inventor
Luther Burbank
By Elizabeth Waters Burbank
Executrix of the Estate of
Luther Burbank, deceased
By Robb & Robb
Attorneys Patented Sept. 6, 1938

Plant Pat. 291

UNITED STATES PATENT OFFICE

291

PEACH TREE

Luther Burbank, deceased, late of Santa Rosa, Calif., by Elizabeth Waters Burbank, executrix, Santa Rosa, Calif., assignor to Stark Bro's Nurseries & Orchards Company, Louisiana, Mo.

Application December 15, 1937, Serial No. 180,043

1 Claim. (Cl. 47—62)

The present invention relates to a new and distinct variety of double-flowering peach trees, having as its primary objective not only the production of an improved type of tree as to form, but also as to its fruit.

In carrying out the object in view, it was natural to employ the exotic varieties of the Orient, noted for the beauty of their flowering, for crossing with standard occidental stock in order to obtain betterment of the form of the tree and edibility of the fruit.

To this end, there is a double-flowering peach that has been long under cultivation in China and Japan. It is a slender, willowy tree, generally characterized by drooping branches. The blossoms are quite double, resembling little roses, usually ¼ inch in diameter, and are produced in great profusion in either white, pink or deep crimson colors. The fruit is hardly edible, even when cooked, and the tree is dwarf and ill-shaped.

This variety was crossed with the Muir peach and other standard high quality varieties of this country until the present variety herein disclosed was obtained by a process of development and selection, it being characterized by its large sized double flowers and its edible fruit.

This new variety has been asexually reproduced and in each instance came true to form.

The following is a detail description of this new variety:

Tree:

Tree is very strong growing and hardy.

Bloomed in Louisiana, Missouri Test Orchard when Elberta and many other commercial varieties of peach buds were killed and only the hardiest varieties came through uninjured.

Flower:

Large, deep crimson buds opening into crimson double rose-like blossoms, many of which are $2\frac{1}{16}$ inches to 2¼ inches in diameter.

*Flower stems.*—Rather stout, ⅛ to ¼ inch long; green shaded on the exposed side with the color of the calyx. Surface distinctly ridged as it merges into the calyx structure.

*Calyx.*—Rather large, lobes as long as the body of the calyx; broadly rounded, slightly reflexed at the tips, this character appearing on the unopened buds and even on wide open flowers. Color—velvety burnt lake, the lobes with a greenish tinge modified by a gray pubescence (Ridgway's Color Standard).

*Flower buds.*—Globular to oval; outer petals soon reflexed as opening period approaches.—Color—Indian Lake (Ridgway's Color Standard).

*Open flowers.*—Petals—20 to 22, oval to obovate in outline, often deeply emarginate or notched at the tip. All petals somewhat wrinkled and often reflexed, enhancing the effect of doubleness. Inner petals often deformed. Color—spinel red (Ridgway's Color Standard).

*Stamens.*—Generally about 40, almost as long as the petals; filaments white in some flowers, and the same color as petals in others.

*Anthers.*—Small; Pompeian red (Ridgway's Color Standard).

*Pistil.*—Usually shorter than the stamens, sometimes very short. Faintly greenish in color. (This tree has borne several heavy crops of fruit during the years of observation, and is evidently self-fertile.)

Fruit:

*Season.*—Mature to commercial picking state about August 22nd at Santa Rosa, California. Ripe for best flavor about August 30th. Extreme range perhaps September 5th.

*Size.*—Small to medium. Axial diameter—2 inches; longest transverse diameter—2⅛ inches; shortest transverse diameter—$2\frac{1}{16}$ inches.

*Form.*—Round, fairly regular and symmetrical.

*Stem.*—Short, rather large for the size of the fruit; inclined to cling to the surrounding tissues when picked.

*Base of fruit.*—Rather broad, flattened.

*Cavity.*—Broad, rather shallow.

*Suture.*—Beginning in the cavity and extending to the apex or even beyond.

*Apex.*—Small, broadly pointed, usually cleft by the suture and usually inclined away from the suture.

*Surface.*—Somewhat uneven; covered with harsh dense white tomentum, giving the fruit a woolly appearance after handling. The tomentum is rather easily removable.

*Skin.*—Rather thick, but not tough enough to allow it to be pulled from the flesh readily, from which it does not separate easily. Color—pale greenish, with indication of cream or Naples yellow, and faint pinkish blush on the exposed side.

*Flavor.*—Rich, subacid, with some astringency.

*Aroma.*—Pleasing.

*Flesh.*—White, tender; very juicy, but slightly fibrous.

*Stone.*—Entirely free; rounded oval, symmetrical, medium to small for the size of the fruit. Axial diameter—1¼ inches, including a prominent point or beak about $\frac{3}{16}$ inch long. Width—⅞ inch. Thickness—¾ inch. Ventral suture ridged, medium width. Dorsal suture nearly a single ridge, not prominent. Color—brown. Convolutions rather shallow and not numerous. Base narrow, point of attachment to stem very small. Apex rounded in general contour, excepting the obliquely set beak.

What is claimed is:

A new and distinct variety of double-flowering peach tree characterized as to novelty by its hardiness, the large sized double rose-like flowers of deep crimson color followed by edible fruit, substantially as shown and described.

ELIZABETH WATERS BURBANK,
*Executrix of the Estate of Luther Burbank, Deceased.*